(12) United States Patent
Amely-Velez et al.

(10) Patent No.: US 6,535,765 B1
(45) Date of Patent: Mar. 18, 2003

(54) IMPLANTABLE MEDICAL STIMULATION DEVICE HAVING RECONFIGURABLE MEMORY

(75) Inventors: Jorge N. Amely-Velez, Simi Valley, CA (US); Dro Darbidian, Tujunga, CA (US); Steven W. Badelt, Granada Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/877,623

(22) Filed: Jun. 8, 2001

(51) Int. Cl.[7] .............................................. A61N 1/02
(52) U.S. Cl. ...................................................... 607/59
(58) Field of Search ............................ 607/4, 5, 59, 2, 607/9, 27, 30; 711/1, 6, 147, 170, 173

(56) References Cited

U.S. PATENT DOCUMENTS

| | | | |
|---|---|---|---|
| 4,779,187 A | * | 10/1988 | Letwin ........................ 712/229 |
| 5,466,254 A | | 11/1995 | Helland ....................... 607/123 |
| 6,195,107 B1 | * | 2/2001 | Iverson ....................... 711/203 |
| 6,282,450 B1 | * | 8/2001 | Hartlaub et al. .............. 607/59 |

OTHER PUBLICATIONS

Deshmukh, Pramod, MD, et al., Permanent Direct His–Bundle Pacing, A Novel Approach to Cardiac Pacing in Patients with Normal His–Purkinje Activation, Circulation, 101, pp. 869–877 (Feb. 2000).

* cited by examiner

*Primary Examiner*—Kennedy Schaetzle

(57) ABSTRACT

The implantable medical device is provided with typically equal portions of both random access memory (RAM) and read only memory (ROM) and a virtual memory space is defined equal to the amount of memory in one of the memory devices. In a specific example, the RAM and ROM provide 256K of memory each, with the virtual memory space also set to 256K. A zone control register is provided which specifies, for each of a set of predetermined zones within the virtual memory space, whether memory access commands are to be routed to RAM or ROM. Control bits within the zone control register may be reset to permit portions of memory to be remapped from one memory device to the other. By providing RAM and ROM each typically equal in size to the virtual memory space, software for use in the device may be tested and debugged using RAM then transferred to ROM for use in production devices. By providing dual RAM and ROM, software upgrades or software bug fixes are easily performed merely by downloading new software into RAM, then resetting the zone control register to point to RAM, rather than ROM. Additionally, when necessary, the overall virtual memory space may be expanded to encompass both the RAM and ROM thereby permitting access to greater quantities of memory.

35 Claims, 3 Drawing Sheets

IMPLANTABLE MEDICAL STIMULATION DEVICE HAVING RECONFIGURABLE MEMORY

FIELD OF THE INVENTION

The invention generally relates to implantable medical devices and in particular to a memory architecture for use with a microcontroller of an implantable medical device.

BACKGROUND OF THE INVENTION

A wide range of implantable medical stimulation devices are provided for surgical implantation into humans or animals. One common example is the cardiac pacemaker. Another is the implantable cardioverter defibrillator (ICD).

Current state of the art implantable medical devices typically include a microcontroller for controlling the functions of the device such as detecting medical conditions within the patient in which the device is implanted and administering appropriate therapy. Within a pacemaker, for example, the microcontroller monitors the detection of P-waves and R-waves to determine whether an episode of bradycardia has occurred and, if so, administers a pacing pulse to the heart. Within an ICD, for example, the microcontroller analyzes P-waves, R-waves and other electrical signals of the heart to determine if an episode of ventricular fibrillation has occurred and, if so, administers a defibrillation shock to the heart.

In addition to performing functions directed to administering immediate therapy, the microcontroller coordinates all other functions of the implantable device, such as: monitoring the power source of the device to determine if the power source needs to be replaced; switching of the mode of operation of the device from, for example, a single-chambered pacing mode to a dual-chambered pacing mode; and recording events such as detection of P-waves and R-waves mode switching events and the administration of therapy for diagnostic purposes. As implantable medical devices become more and more sophisticated, the number and complexity of functions that must be performed by the microprocessor increases as well. As a result, the software for controlling the microprocessor becomes increasingly complex and the amount of time required to design, test and debug the software also becomes more significant. Indeed, in many cases, the development of reliable software can significantly delay the overall development of a new implantable medical device. Accordingly, it is highly desirable to expedite the development of reliable software for use in an implantable medical device and aspects of the invention are directed to that general goal.

Typically, software is developed using random access memory (RAM) devices that can be programmed and reprogrammed many times during the development of the software. To reliably test the device, the software should be used in conjunction with the entire implantable medical device. Also, while testing software within the test device, it is also desirable to test various hardware components of the device, such as pulse generators, sensors and the like. Hence, test devices are built which incorporate all of the hardware of the implantable medical device with RAM chips for storing the software to be tested. Ideally, however, the final medical device incorporates read only memory (ROM) rather than RAM to reduce power consumption, increase processing speed, and prevent any corruption of the software, as may occur as a result of a power surge or perhaps as a result of the malfunction of some other component of the device, such as the microprocessor. However, the use of RAM during software design and test, rather than ROM, may affect the amount of current consumed by the device, or other device characteristics, possibly resulting in invalid tests of the hardware components of the device. For example, after the software is embodied in ROM for installation into a production device, the slight difference in current consumption caused by switching from RAM to ROM may result in sense amplifiers not operating precisely as expected. Moreover, in many cases, while software is being developed, the amount of memory required by the software exceeds the amount of memory expected to be used in the production device. As a result, to test intermediate versions of the software, additional RAM chips are used in the test device, further affecting the total current consumption, resulting in a still greater risk that the hardware components of the device, once RAM is replaced with ROM in the production device, will not operate precisely as expected.

Accordingly, it would be highly desirable to provide an improved method for designing, testing and debugging software for use in an implantable medical device and an improved device for receiving the software, which overcomes the aforementioned disadvantages. It is to this end that many aspects of the invention are specifically directed.

Another problem associated with employing ROM memory in the production unit of an implantable medical device, is that software upgrades or software bug fixes cannot easily be performed. Indeed, if the software to be upgraded or fixed resides within ROM, the ROM may need to be replaced, requiring explantation of the implanted device from a patient, then implantation of a new or modified device. As can be appreciated, this is a considerable inconvenience to the patient and a significant cost to the manufacturer of the device. Accordingly, it would also be desirable to provide a hardware memory configuration for use in the production unit of implantable medical devices, which facilitates expedient software upgrades or software bug fixes, and still other aspects of the invention are directed towards that goal.

SUMMARY OF THE INVENTION

In accordance with the invention, a memory system is provided for use in an implantable medical device having various computing components accessing a virtual memory space corresponding to a predetermined amount of memory. The memory system includes dynamic means for storing data, permanent means for storing data, and a memory controller means for mapping portions of the virtual memory space to either the dynamic means for storing data or the permanent means for storing data.

In an exemplary embodiment, the implantable medical device is a pacemaker or implantable cardioverter defibrillator. The dynamic storage means is RAM and the permanent storage means is ROM. The memory controller means includes a zone control register that specifies, for each of a predetermined number of zones of virtual memory, whether the zone is to be mapped to RAM or ROM. The zone control register is a binary register having one bit per memory zone with the bit set to indicate either ROM or RAM. In one specific implementation, the predetermined amount of memory of the virtual memory space is 256 kilobytes (256K) of memory. The RAM and ROM each provide 256K of memory as well, permitting the entire virtual memory space to be mapped either to RAM or ROM.

By providing the implantable medical device with both RAM and ROM, software for use in the device can be stored in the RAM while software is being designed, tested and debugged. Then, once the software design has been finalized, the final software design is embodied in ROM. In this manner, the actual production unit of the device may exploit the benefits of the ROM whereas testing may be performed while obtaining the benefits of RAM, without changing power consumption requirements or other device characteristics. Hence, both the software and hardware components of the implantable medical device can be reliably tested without risk that slight changes in current consumption caused by replacing RAM with ROM may invalidate the tests. Also, by providing each production unit with both RAM and ROM, software upgrades may be accomplished easily by downloading new software into a portion of the RAM, then controlling the memory controller means to map portions of the virtual memory space to access the RAM rather than the ROM. In this manner, any software bugs discovered in the software of the ROM may be easily corrected without requiring replacement of the ROM which, in the case of an implantable medical device, would likely require explantation of the device from the patient.

Other objects and advantages of the invention are achieved as well. Method embodiments of the invention are also provided.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

The description is of a system having an implantable cardiac stimulation device for implantation into a patient.

Figure 1:
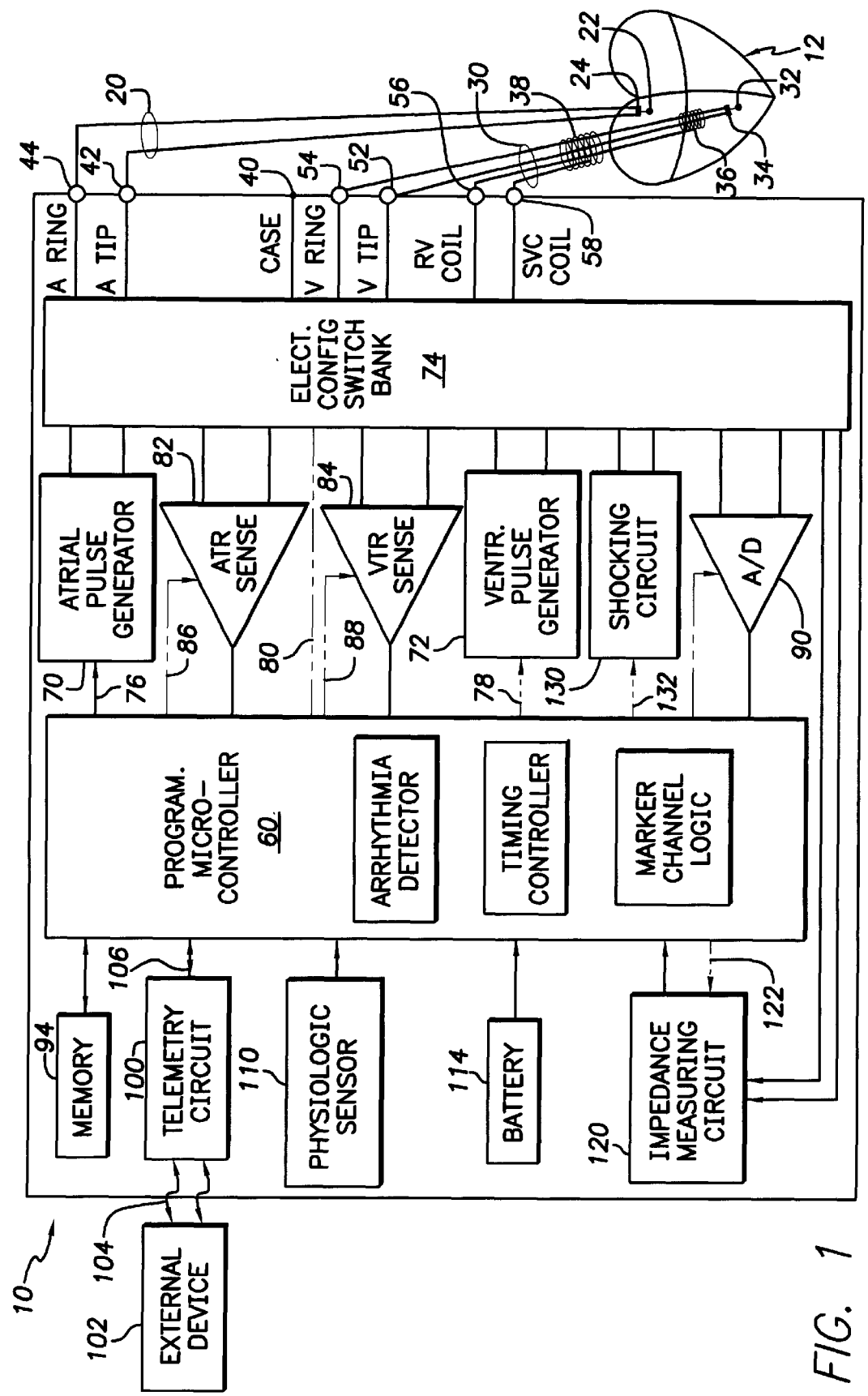
FIG. 1 is a functional block diagram of a dual-chamber implantable stimulation device illustrating the basic elements of a stimulation device, which can provide cardioversion, defibrillation and pacing stimulation.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an superior vena cava (SVC) coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. patent application Ser. No. 09/457,277, "A Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

At the core of the stimulation device 10 is a programmable microcontroller 60, which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses as known in the art. The controller also includes an auto-capture threshold detection system described in greater detail below.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation. The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers.

For arrhythmia detection, the invention utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P-P, P-R and R-R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 (to be described in greater detail below) by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Memory 94 also stores software to be loaded into the microcontroller for controlling the operation of the microcontroller.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 may be activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the invention and is shown only for completeness. The stimulation device additionally includes a battery 114 that provides operating power to all of the circuits shown in FIG. 1. For the stimulation device 10, which employs shocking therapy, the battery must be capable of operating at low current drains for long periods of time, and then be capable of providing high-current pulses (for capacitor charging) when the patient requires a shock pulse. The battery 114 must also have a predictable discharge characteristic so that elective replacement time can be detected. As further shown in FIG. 1, the invention preferably includes an impedance measuring circuit 120, which is enabled by the microcontroller 60 by a control signal 122. The impedance measuring circuit 120 is not critical to the invention and is shown for only completeness.

Depending upon the implementation, the device may function as an implantable cardioverter/defibrillator (ICD) device. In the case where the stimulation device 10 in intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 2:
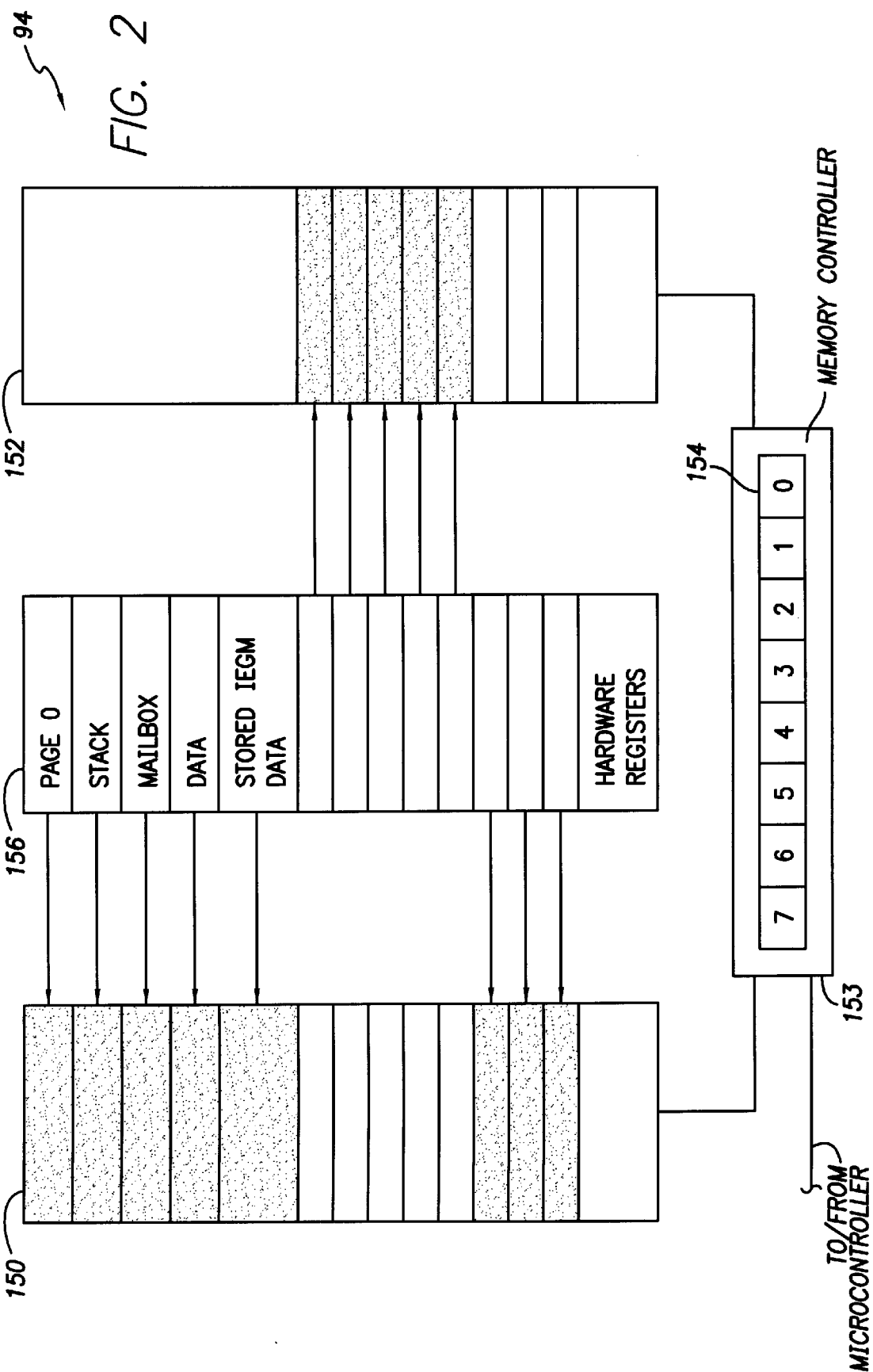
FIG. 2 illustrates a memory configuration for use with the implantable device of FIG. 1.

FIG. 2 illustrates and exemplary implementation of memory 94 of the implantable device of FIG. 1. Memory 94 includes, but is not limited to, static or dynamic RAM 150, ROM 152 or other static memory and a memory controller 153 having a zone control register 154 which specifies, for each of eight memory zones, whether memory access commands received from microcontroller 60 (FIG. 1) are to be directed to RAM or ROM. In other examples, more or fewer memory zones may be employed. FIG. 2 also illustrates an exemplary virtual memory space map 156 having various memory zones. In the example of FIG. 2, the memory map covers 256K of memory. RAM 150 and ROM 152 each provide 256K of physical memory for a total of 512K. Zone control register 154 includes bits set to specify whether virtual memory within each of the predefined zones is mapped to RAM or ROM. To this end, the zone control register includes a sequence of eight bits, one bit for each of the eight predefined zones. If the zone control register bit for a zone is set to 1, all memory access commands specifying memory locations within that zone are routed to the RAM. If the bit is set to 0, then all memory access commands accessing memory within the zone are routed to ROM. The specific sequence of bits within the zone control register is set by the microcontroller or external device 102 based upon software operating therein.

Thus, 512K of physical memory is provided to correspond with 256K of virtual memory accessible by the microcontroller. With this implementation, software being developed is stored within RAM for the purposes of testing the operation of the software and the overall device. During testing, each of the bits of the zone control register is set to specify the RAM. Hence, during testing, all memory access commands of the microcontroller are automatically routed to RAM. Once the implantable device has been fully tested and all software and hardware components are functioning properly, the final version of software within the RAM is transferred to ROM, i.e., the ROM is hardwired to embody the final software design. Then, selected bits of the zone control register are reset to direct memory access commands to the ROM.

In this manner, the benefits of RAM are exploited during design, test, and debug of the implantable device, whereas the benefits of ROM are exploited within production copies of the device. More specifically, the dynamic capability of RAM is exploited during software development to permit the software to be repeatedly changed until any software bugs have been eliminated and the software is functioning properly. Moreover, if any changes to the hardware of the device are made during device development, which necessitate changes in software, the software can be readily changed or upgraded to accommodate the modified hardware. Within production units, however, the static storage aspect of ROM is exploited to ensure that the software of the production device cannot be accidentally corrupted or otherwise improperly modified, perhaps as a result of power surges within the implanted device or as a result of any software bugs which might corrupt software stored within RAM. Hence, the advantages of RAM and ROM storage devices are both exploited. Moreover, because the actual production device contains both RAM and ROM, the problems described above that can arise when switching from RAM chips within a test device to ROM chips within a production device are avoided, particularly problems arising when the number of RAM chips used during test is greater than the number of ROM chips used in the production device.

Another advantage of employing both RAM and ROM in the final production device is that, if software bugs are detected within the software incorporated within ROM, corrected software can be loaded into RAM, and the appropriate bits of the zone control register reset to reference the corrected software. For example, if a software bug is detected within software within zone 3 of the virtual memory map, corrected software is downloaded into zone 3 of the RAM from an external programmer via a telemetry unit and the bit within the zone control register corresponding to zone 3 is reset to identify RAM. Thereafter, whenever the microcontroller accesses memory locations within zone 3, the memory access commands are automatically routed to RAM rather than ROM, thereby avoiding the defective software. Hence, software bug fixes are performed without requiring explantation of the device. As can be appreciated, if all software were stored only within ROM, the implanted device would need to be removed from the patient so that the ROM could be replaced with ROM containing corrected software.

Thus, selected portions of the virtual memory space are routed to either RAM or ROM depending upon the bits within the zone control register. However, any portions of memory that must remain dynamic are stored only within RAM. In one specific implementation, portions of the virtual memory space of the implantable device correspond with page zero, stack, mailbox, data and stored EIGM information. As this information is dynamic, memory zones containing the dynamic information are always routed to RAM. In one possible example, the page zero zone stores information for use in booting the microcontroller following a reset and may store dynamic status information and the like from a preceding session. Within the page zero zone, a copy of the zone control register bits may be stored to permit the device to reset with proper zone control bits. The stack zone provides a memory area for storing dynamic information used by software operating within the microcontroller. The mailbox zone provides for storage of certain types of communication information received from the external programmer. The data zone accommodates data used by the microcontroller during its operation and may store, for example, counts of the number of various events detected by the microcontroller, such as mode switching events, paced events, sensed events and the like. The stored IEGM data zone stores IEGM signals detected by the device while the device is operating to permit subsequent review by a physician during a follow-up session with the patient. Other uses may be provided for these various zones. For example, the page zero zone need not be used to store information for use in booting the microcontroller. Moreover, in other implementations, more or fewer zones may be exclusively mapped to RAM. The other zones not specifically labeled in FIG. 2 may be mapped to either RAM or ROM. Typically, these other zones store the actual operational software of the device for loading into the microcontroller subsequent to a reset or during an initial power up operation.

Another advantage of providing both RAM and ROM is that the overall virtual memory space for the device can be expanded to encompass both the RAM and the ROM. In the example wherein RAM and ROM both provide 256K of memory, the entire memory space may be expanded to as much as 512K by exploiting both RAM and ROM. Thus, for example, if a software upgrade is to be provided within the device, but the new software requires a greater amount of memory than can be accommodated within a total memory space of 256K, portions of RAM and ROM can be designated as both being accessible thereby expanding the overall memory space beyond 256K. This requires appropriate modification to the software controlling the zone control register to permit access to corresponding zones within both RAM and ROM. In this regard, the bits within the zone control register are dynamically controlled to switch back and forth between RAM and ROM. As one specific example, during a power up operation, various zone control bits may be set to point to ROM to permit software to be uploaded into the microcontroller from ROM. Then, once the software is operating within the microcontroller, the corresponding bits of the zone control register are set to RAM to permit the microcontroller to exploit the corresponding portion of RAM memory as dynamic memory for use in storing, for example, IEGM data or the like.

In other implementations, rather than using RAM as the dynamic memory, flash memory or electrically erasable and programmable ROM (EEPROM) is employed. Other types of static memory may alternatively be employed besides ROM. Also, although described with respect to an example wherein a single virtual memory space is employed, the principles of the invention may also be exploited within devices employing multiple virtual memory spaces and multiple corresponding physical memory devices. This may be desirable, for example, in devices having multiple microcontrollers. For example, a memory system may be provided generally as shown in FIG. 2 but with two sets of virtual memory spaces, each having corresponding RAM and ROM portions.

Figure 3:
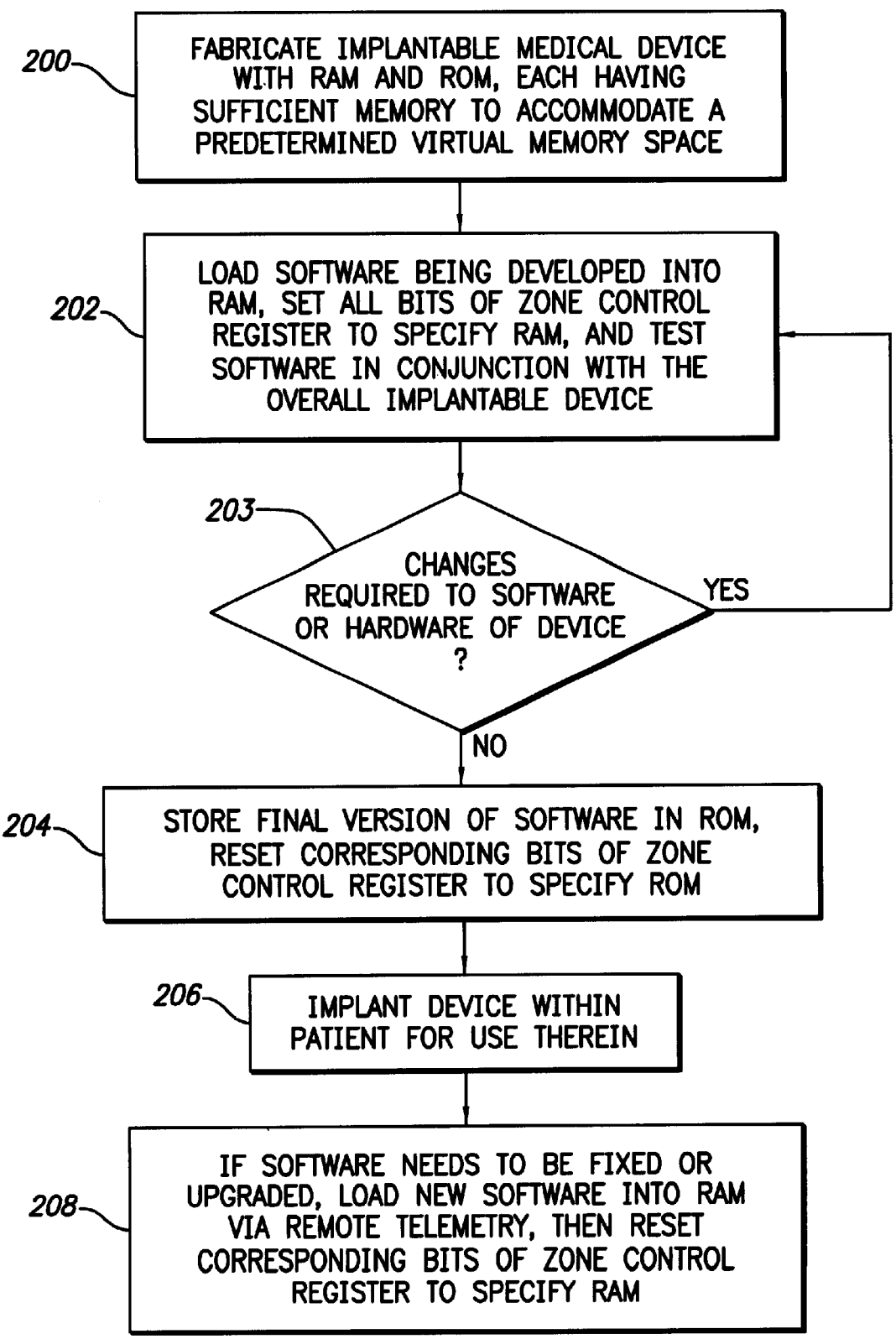
FIG. 3 is a flow chart illustrating a method for use with the memory configuration of FIG. 2.

General operations performed using the dual RAM and ROM illustrated in FIG. 2 will now be briefly summarized with reference to the flow chart of FIG. 3. At step 200, an implantable medical device is fabricated having both RAM and ROM. At step 202, software under development is loaded within RAM and tested. If changes need to be made to the software, step 203, new software is loaded into the RAM at step 202. Otherwise, at step 204, the final production version of software is encoded within ROM. At step 206, the device is implanted within a patient for use therein. If, at step 208, the software needs to be upgraded, new software is downloaded into RAM at step 210 and the appropriate zone control register bits are reset to point to RAM.

The various functional components of the exemplary system may be implemented using any appropriate technology including, for example, microprocessors running software programs or application specific integrated circuits (ASICs) executing hard-wired logic operations. Although described primarily with respect to an ICD used in conjunction with an external programmer, aspects of the invention are applicable to other systems, such as systems employing other implantable medical devices or systems employing other types of external interfaces for use with the implantable device. The exemplary embodiments of the invention described herein are merely illustrative of the invention and should not be construed as limiting the scope of the invention.

What is claimed is:

1. In an implantable medical device having various computing components accessing a virtual memory space corresponding to a predetermined amount of memory, a memory system comprising:

dynamic memory means for dynamically storing data, the dynamic memory means corresponding in size to at least the predetermined amount of memory;

permanent memory means for statically storing data, the permanent memory means also corresponding in size to at least the predetermined amount of memory; and memory controller means for dynamically mapping selected portions of the virtual memory space to either the dynamic memory means or the permanent memory means, such that the entire virtual memory space can be mapped, if needed, to either just the dynamic memory means or to just the static memory means.

2. The memory system of claim 1 wherein the dynamic memory means is a RAM, flash memory or EEPROM.

3. The memory system of claim 1 wherein the permanent memory means is a ROM.

4. The memory system of claim 1 wherein the memory controller means is preprogrammed to always map certain predetermined portions of the virtual memory to the dynamic memory means.

5. The memory system of claim 4 wherein the predetermined portions of the virtual memory space include portions requiring dynamic access.

6. The memory system of claim 5 wherein the portions requiring dynamic access include one or more of portions dedicated to storing page zero information, stack information, mailbox information, patient data and stored internal electrocardiogram (IEGM) data.

7. The memory system of claim 1 wherein the memory controller includes a means for specifying, for each of a predetermined number of zones of the virtual memory, whether the memory is mapped to the dynamic memory means or the permanent memory means.

8. The memory system of claim 7 wherein the means for specifying whether the memory is mapped to dynamic memory means or permanent memory means is a zone control register.

9. The memory system of claim 8 wherein the zone control register is a binary register having one bit per predetermined memory zone, the bit set to a first binary value to indicate the dynamic memory means and to a second binary value to indicate the permanent memory means.

10. The memory system of claim 1 wherein the memory controller means receives an indication of a corrupted portion of memory within the dynamic memory means or the permanent memory means and re-maps the portion of the virtual memory space previously mapped to the corrupted portion of memory to a corresponding portion of memory in the other memory means.

11. The memory system of claim 1 wherein the memory controller means receives updated data for replacing a portion of data of the permanent memory means, stores the updated data within the dynamic memory means, and re-maps the virtual memory space to access the updated data of the dynamic memory means.

12. The memory system of claim 11 wherein the updated data includes software.

13. The memory system of claim 1 wherein the memory controller means receives an indication of data of the permanent memory means to be accessed instead of data of the dynamic memory means and re-maps the virtual memory space to access the data of the permanent memory means instead of data of the dynamic memory means.

14. The memory system of claim 1 wherein virtual memory space exceeds the predetermined amount of memory and wherein the memory controller means maps memory addresses lying within the virtual memory space but outside of the predetermined amount of memory to the portions of the dynamic memory means not mapped by the memory controller means.

15. The memory system of claim 1 for use within an implantable medical device selected from a group including a pacemaker and an implantable cardioverter defibrillator (ICD).

16. The memory system of claim 1 for use within an implantable medical device having various computing components accessing two or more virtual memory spaces.

17. In an implantable medical device, a memory system comprising:
   a controller accessing a virtual memory space corresponding to a predetermined amount of memory;
   a dynamic memory unit corresponding in size to at least the predetermined amount of memory;
   a permanent memory unit also corresponding in size to at least the predetermined amount of memory; and
   memory controller dynamically mapping selected portions of the virtual memory space to either the dynamic memory unit or the permanent memory unit, such that the entire virtual memory space can be mapped, if needed, to either just the dynamic memory unit or to just the static memory unit.

18. The memory system of claim 17 wherein the dynamic memory unit is a RAM, flash memory or EEPROM.

19. The memory system of claim 17 wherein the permanent memory unit is a ROM.

20. The memory system of claim 17 wherein the memory controller is preprogrammed to always map certain predetermined portions of the virtual memory to dynamic memory unit.

21. The memory system of claim 20 wherein the predetermined portions of the virtual memory space include portions requiring dynamic access.

22. The memory system of claim 21 wherein the portions requiring dynamic access include one or more of portions dedicated to storing page zero information, stack information, mailbox information, patient data and stored internal electrocardiogram (IEGM) data.

23. The memory system of claim 17 wherein the memory controller specifies, for each of a predetermined number of zones of the virtual memory, whether the memory is mapped to the dynamic memory unit or the permanent memory unit.

24. The memory system of claim 23 wherein the memory controller includes a zone control register.

25. The memory system of claim 24 wherein the zone control register is a binary register having one bit per predetermined memory zone, the bit set to a first binary value to indicate the dynamic memory unit and to a second binary value to indicate the permanent memory unit.

26. The memory system of claim 17 wherein the memory controller receives an indication of a corrupted portion of memory within the dynamic memory unit or the permanent memory unit and re-maps the portion of the virtual memory space previously mapped to the corrupted portion of memory to a corresponding portion of memory in the other memory unit.

27. The memory system of claim 17 wherein the memory controller receives updated data for replacing a portion of data of the permanent memory unit, stores the updated data within the dynamic memory unit, and re-maps the virtual memory space to access the updated data of the dynamic memory unit.

28. The memory system of claim 27 wherein the updated data includes software.

29. The memory system of claim 17 wherein the memory controller receives an indication of data of the permanent memory unit to be accessed instead of data of the dynamic memory unit and re-maps the virtual memory space to access the data of the permanent memory unit instead of data of the dynamic memory unit.

30. The memory system of claim 17 wherein virtual memory space exceeds the predetermined amount of memory and wherein the memory controller maps memory addresses lying within the virtual memory space but outside of the predetermined amount of memory to the portions of the dynamic memory unit not mapped by the memory controller.

31. The memory system of claim 17 for use within an implantable medical device selected from a group including a pacemaker and an implantable cardioverter defibrillator (ICD).

32. The memory system of claim 17 for use within an implantable medical device having various computing components accessing two or more virtual memory spaces.

33. In an implantable medical device having a microcontroller capable of accessing a virtual memory space, a memory system including a dynamic memory unit and a static memory unit, with each memory unit having sufficient memory to accommodate the entire virtual memory space, and a memory controller for dynamically mapping selected portions of the virtual memory space to either the dynamic memory unit or the static memory unit, a method for controlling memory access comprising the steps of:
   storing control software in the static memory unit and configuring the memory controller to map portions of the virtual memory space corresponding to control software to the static memory unit;
   storing data in the dynamic memory unit and configuring the memory controller to map portions of the virtual memory space corresponding to data to the dynamic memory unit;
   receiving a memory access command from the microcontroller specifying a virtual memory address;
   determining, using the memory controller, whether the virtual memory address is currently mapped to the dynamic memory unit or the static memory unit; and
   forwarding the memory access command to the respective memory unit for accessing memory therein.

34. The method of claim 33 further comprising the steps of:
   storing modified control software in the dynamic memory unit; and
   configuring the memory controller to re-map portions of the virtual memory space corresponding to the updated control software to the dynamic memory unit instead of to the static memory unit such that subsequent memory access commands to virtual memory addresses corresponding to the modified control software are automatically directed to the dynamic memory unit rather than to the static memory unit.

35. The method of claim 33 further comprising the steps of:
   configuring the microcontroller to access a larger virtual memory space than accommodated by either the dynamic memory unit or the static memory unit alone; and
   configuring the memory controller to map a first portion of the larger virtual memory space to the static memory unit and a second portion of the larger virtual memory space to the dynamic memory unit such that subsequent memory access commands to the first portion of the virtual memory space are automatically directed to the static memory unit and subsequent memory access commands to the second portion of the virtual memory space are automatically directed to the dynamic memory unit.

* * * * *